US00PP35421P2

(12) United States Plant Patent
Yori

(10) Patent No.: US PP35,421 P2
(45) Date of Patent: Oct. 17, 2023

(54) ALMOND TREE NAMED 'PY1'

(50) Latin Name: *Prunus dulcis*
Varietal Denomination: PY1

(71) Applicant: Phillip Martin Yori, Ceres, CA (US)

(72) Inventor: Phillip Martin Yori, Ceres, CA (US)

( * ) Notice: Subject to any disclaimer, the term of this patent is extended or adjusted under 35 U.S.C. 154(b) by 0 days.

(21) Appl. No.: 17/667,420

(22) Filed: Feb. 8, 2022

(51) Int. Cl.
*A01H 5/08* (2018.01)
*A01H 6/74* (2018.01)

(52) U.S. Cl.
USPC ..... Plt./155
CPC ..... *A01H 6/7427* (2018.05)

(58) Field of Classification Search
USPC ..... Plt./155
CPC ..... A01H 5/0825; A01H 5/0837
See application file for complete search history.

(56) References Cited

U.S. PATENT DOCUMENTS

| | | | |
|---|---|---|---|
| PP2,641 | P | 6/1966 | Arakaki |
| PP3,483 | P | 2/1974 | Stretch et al. |
| PP13,286 | P3 | 11/2002 | Kester et al. |
| PP26,083 | P3 | 11/2015 | Bennett |
| PP32,301 | P2 | 10/2020 | Slaughter |

*Primary Examiner* — Kent L Bell
(74) *Attorney, Agent, or Firm* — Sierra IP Law, PC; Mark D. Miller

(57) ABSTRACT

The present invention provides a new and distinct variety of almond tree, named 'PY1', substantially as described and illustrated herein, that is a pollinator for existing varieties, and which produces nuts with rare doubles that are similar to existing varieties, with a crop having a fresh earthy taste, that is well suited for roasting, seasoning, oil and flavoring.

13 Drawing Sheets

Latin name: *Prunus dulcis.*
Varietal denomination: 'PY1'.

BACKGROUND OF THE NEW VARIETY

The present invention relates to a new and distinct variety of almond tree, botanically know as *Prunus dulcis*, which will hereby be denominated by the cultivar name 'PY1', and more specifically to an almond tree that produces a crop for harvesting in late August and shipment in early September under the ecological conditions prevailing in the Stanislaus County area of the San Joaquin Valley of central California.

'PY1' was discovered in 2001 as a seedling growing adjacent to an orchard of 'Nonpareil' (unpatented), 'Carmel' (U.S. Plant Pat. No. 2,641), and 'Peerless' (unpatented) almond trees close to the property line on the inventor's property located in Stanislaus County, California, in the San Joaquin Valley. The variety has been observed to provide nuts that are similar to the non-patented 'Nonpareil' variety and the 'Monterey' variety (U.S. Plant Pat. No. 3,483). Asexual reproduction of the tree has produced progeny that are consistent with the original specimen as to vegetative characteristics.

ORIGIN AND ASEXUAL REPRODUCTION

The variety was discovered by the inventor as a volunteer seedling adjacent to an orchard of 'Nonpareil' (unpatented), 'Carmel' (U.S. Plant Pat. No. 2,641), and 'Peerless' (unpatented) almond trees close to the property line on the inventor's property located in Stanislaus County, California. The original seedling was asexually reproduced in 2001 in Stanislaus County, California by collecting budwood from the mother tree that was budded onto 18 trees on unpatented 'Nemaguard' and other rootstocks. All of these trees have survived.

Reproduction by budding and grafting resulted in true-to-type progeny with respect to all tree vegetative and reproductive characteristics. These reproductions utilized unpatented 'Nemaguard' rootstock on which the present variety was compatible and true to the original tree in all respects.

The presently observed reproduced specimens are now in their 20th leaf.

SUMMARY OF THE VARIETY

The present variety was selected and tested because of its unique nut production and has the following outstanding and distinguishing characteristics when grown under normal horticultural practices in the Stanislaus County area of the San Joaquin Valley of central California. The harvest date of 'PY1' is just after that of unpatented 'Nonpareil'. Nut yield of the new variety is on average slightly greater than that of the unpatented 'Nonpareil' variety, and nut quality is comparable to 'Monterey' (U.S. Plant Pat. No. 3,483). The variety blooms about 2 days earlier than unpatented 'Nonpareil', has an abundance of flowers along each fruiting branch, and stops blooming about 4 days earlier than unpatented 'Nonpareil'. The present variety is a good pollinator for use with 'Monterey' (U.S. Plant Pat. No. 3,483) and unpatented 'Dallas' varieties.

DESCRIPTION OF THE PHOTOGRAPHS

The branches, nuts, foliage and flowers of the new almond variety are illustrated by the accompanying color photographs. The samples depicted in the photographs are taken from trees that are in their 20th year, grown utilizing unpatented 'Nemaguard' rootstock, under the ecological conditions prevailing in the Stanislaus County area of the San Joaquin Valley of central California.

Figure 1:
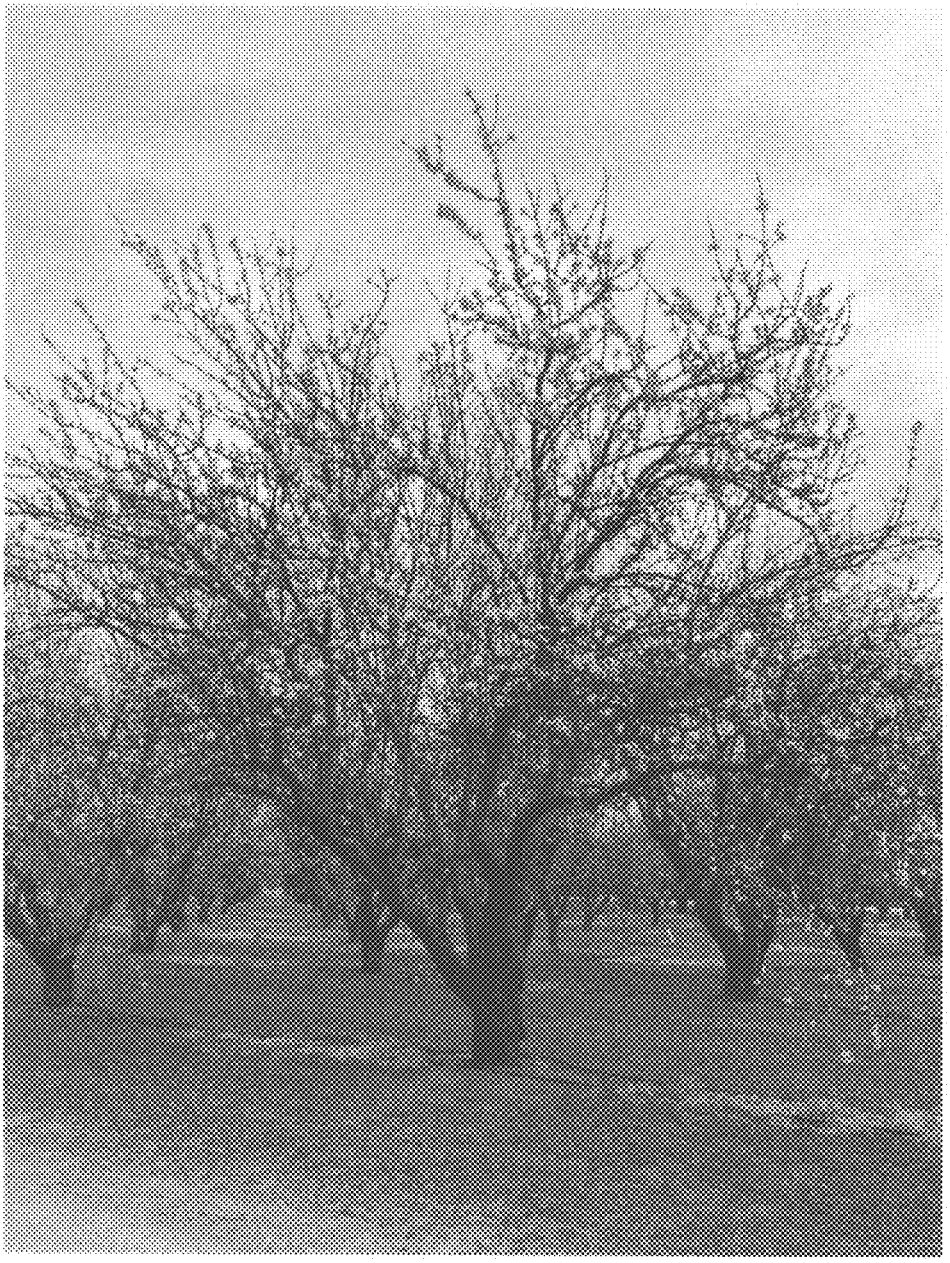
FIG. 1 is a view of a tree of the present variety in bloom in February.
Figure 2:
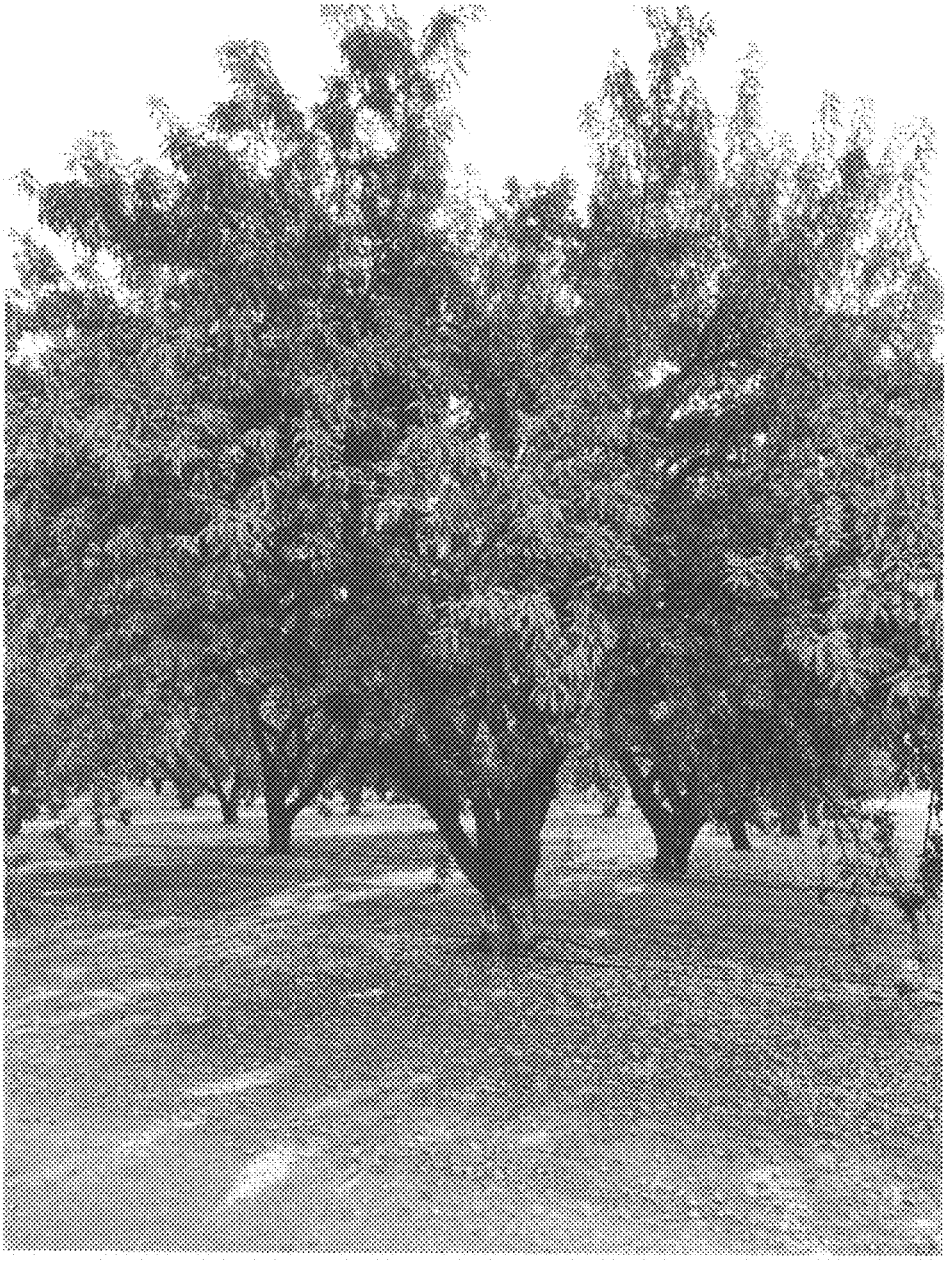
FIG. 2 is a view of a tree of the present variety laden with nuts in August.
Figure 3:
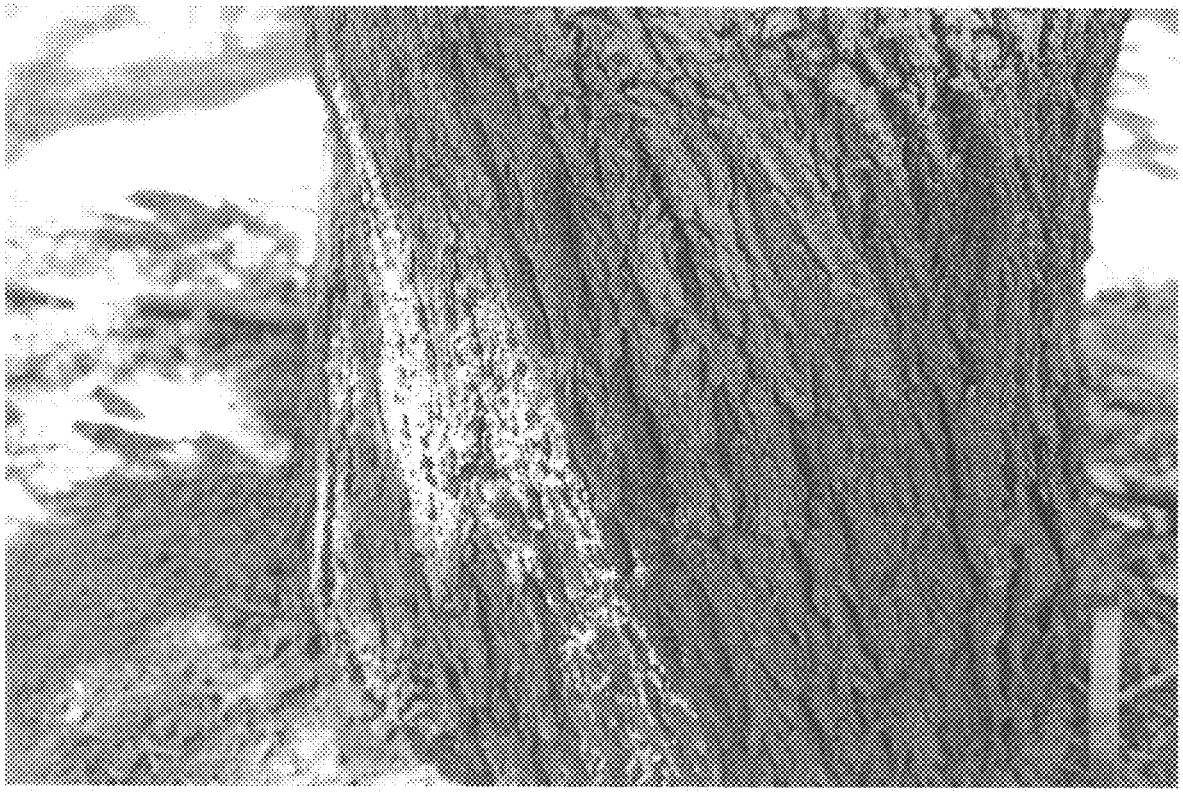
FIG. 3 is a close-up view of a trunk of a tree of the new variety.
Figure 4:
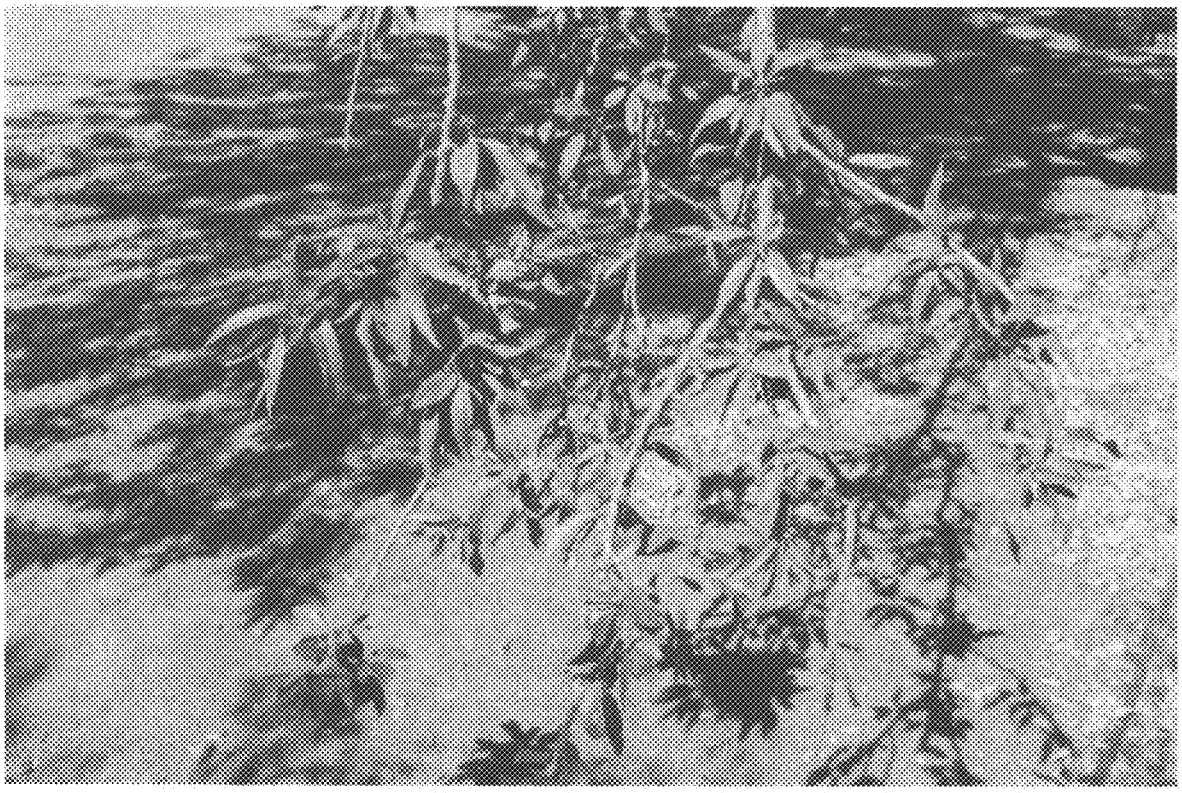
FIG. 4 is a close-up view of leaves and branches of the new variety in situ.
Figure 5:
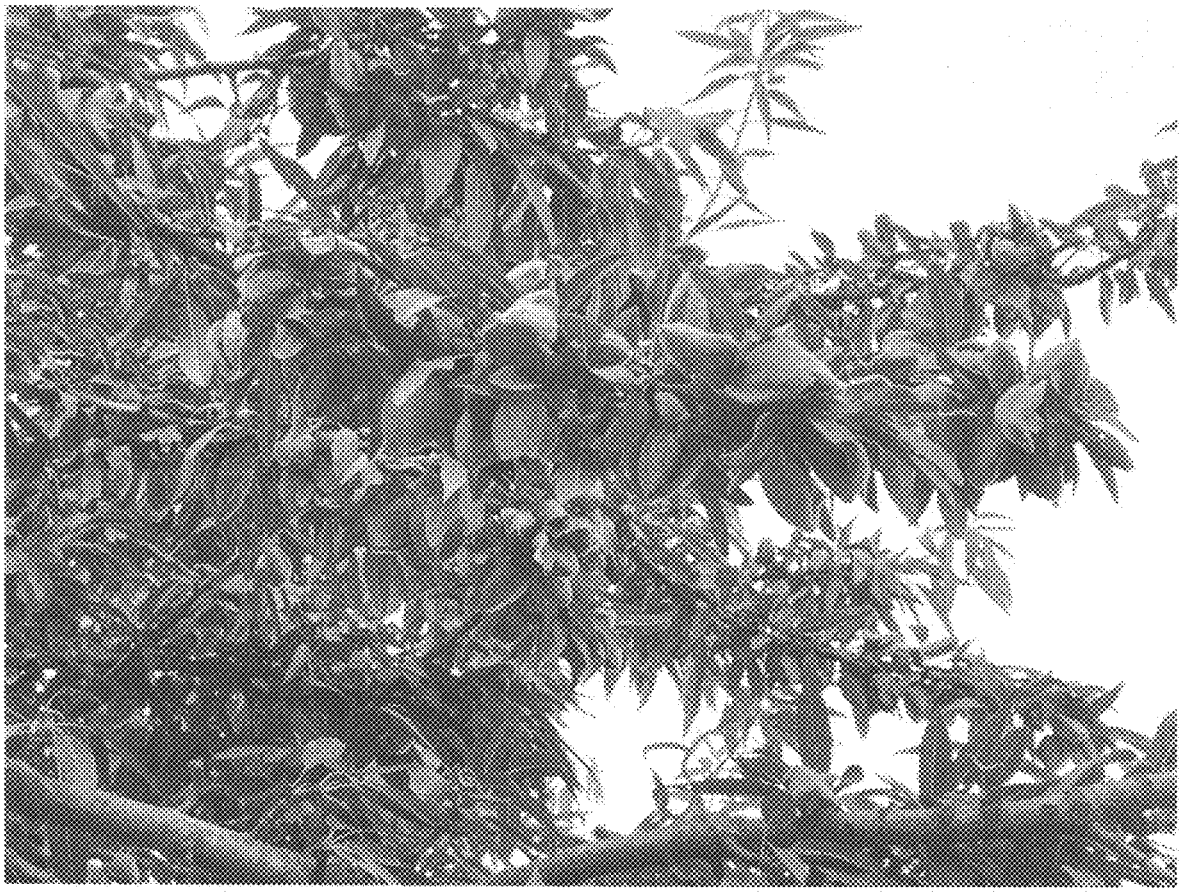
FIG. 5 is a view of mature nuts in situ on tree branches of the new variety just prior to harvest.
Figure 6:
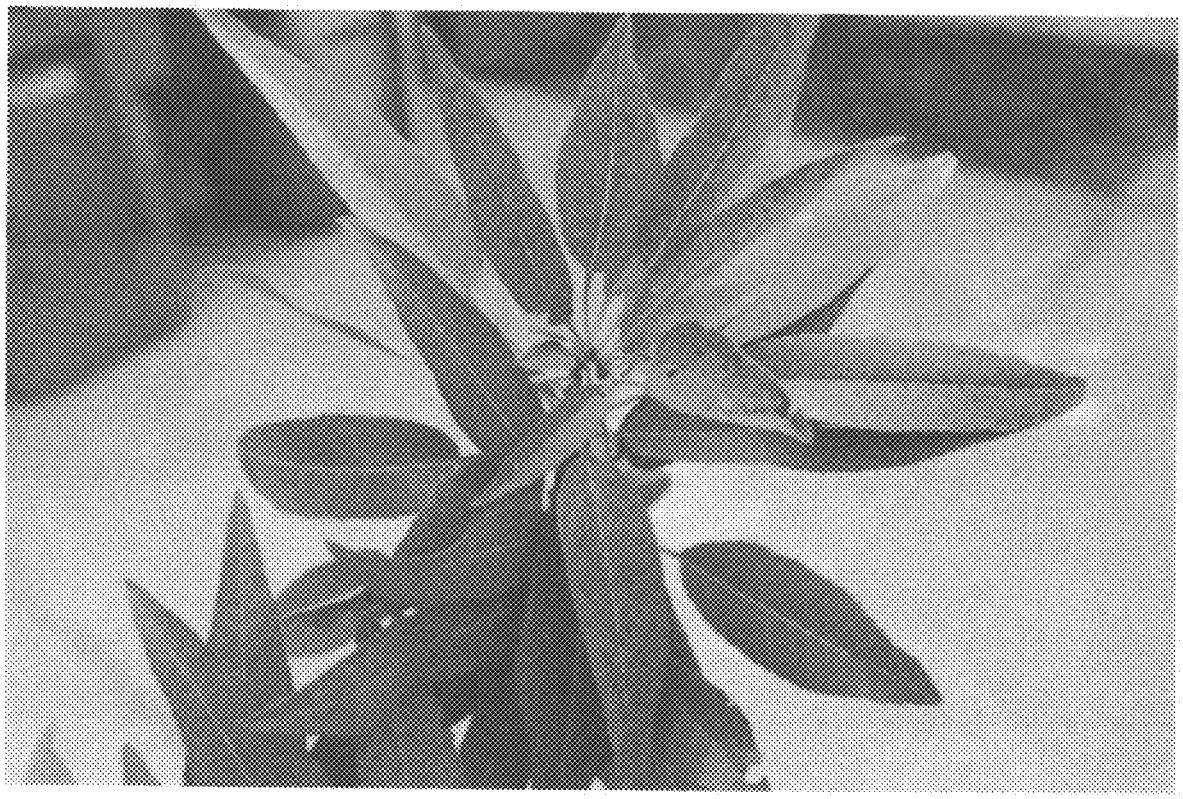
FIG. 6 is a close-up top view of foliage of the new variety.
Figure 7:
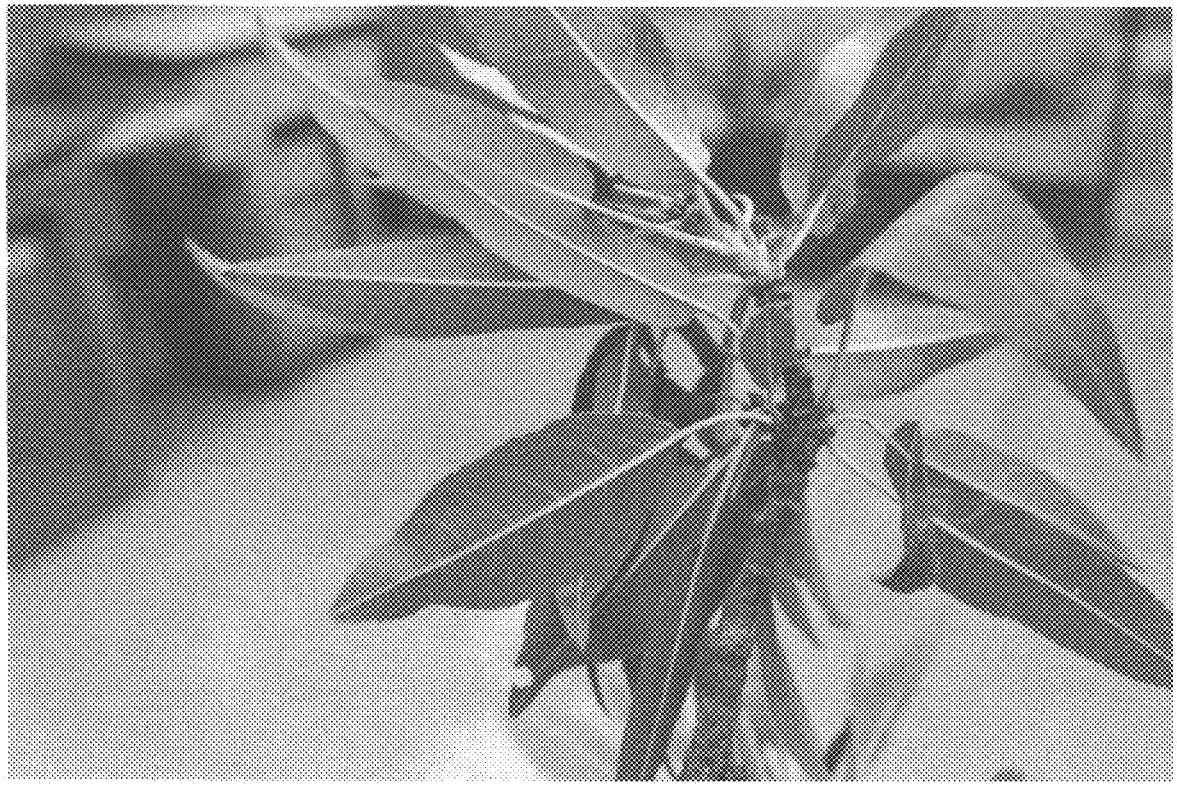
FIG. 7 is a close-up underneath view of foliage of the new variety.
Figure 8:
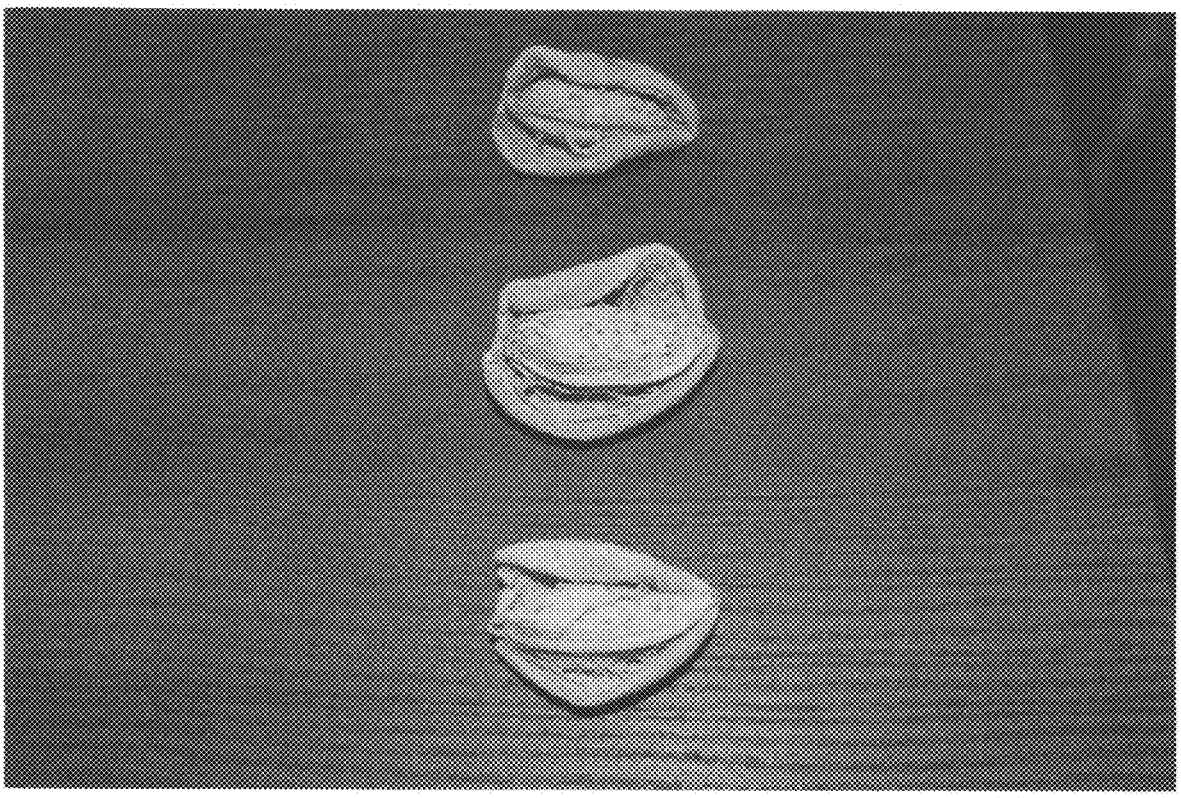
FIG. 8 is a close-up view of hulls with shells and nuts of the new variety.
Figure 9:
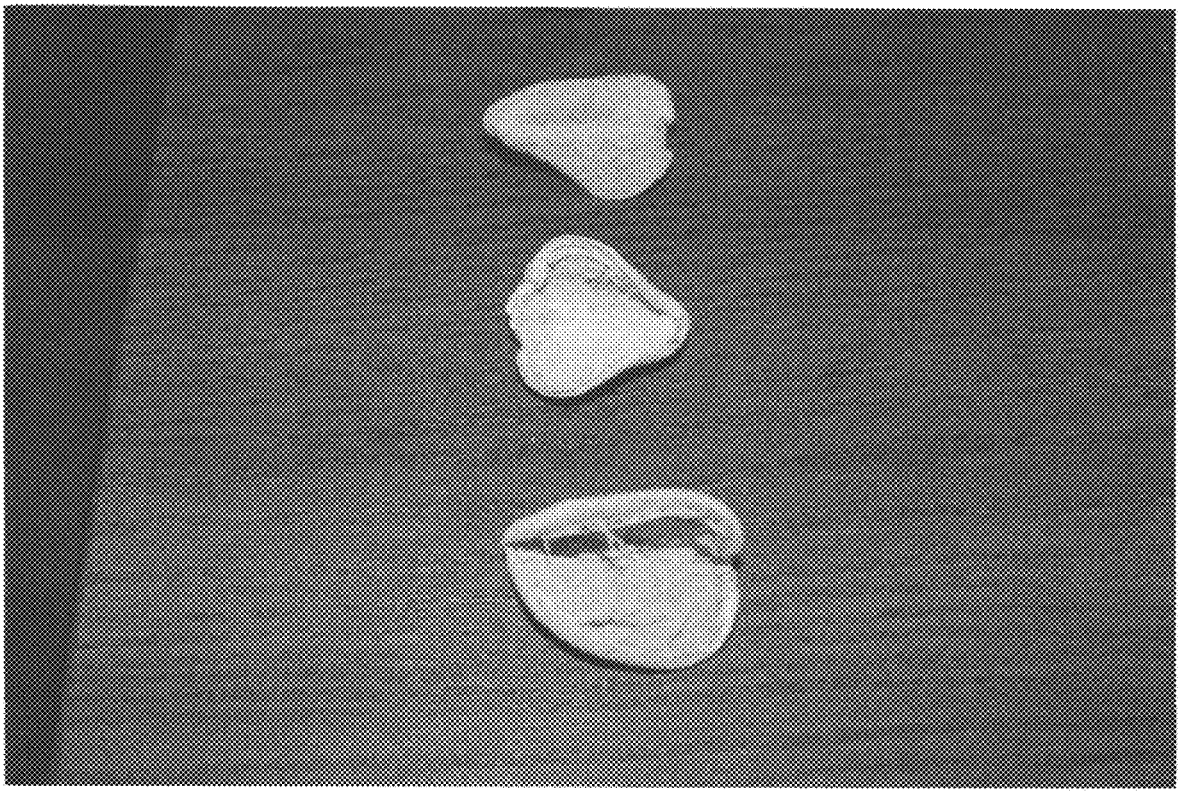
FIG. 9 is a close-up view of hulls of the new variety from which shells have been removed.
Figure 10:
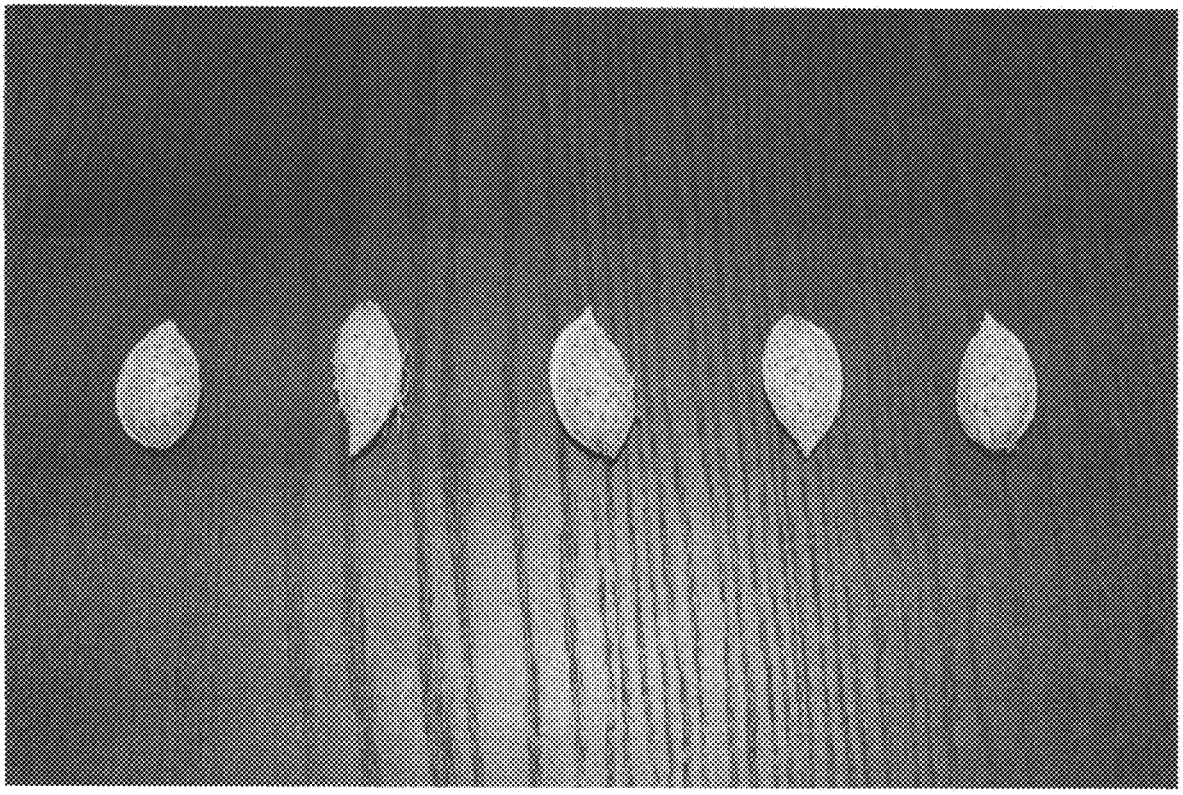
FIG. 10 is a close-up view of shells of the new variety.
Figure 11:
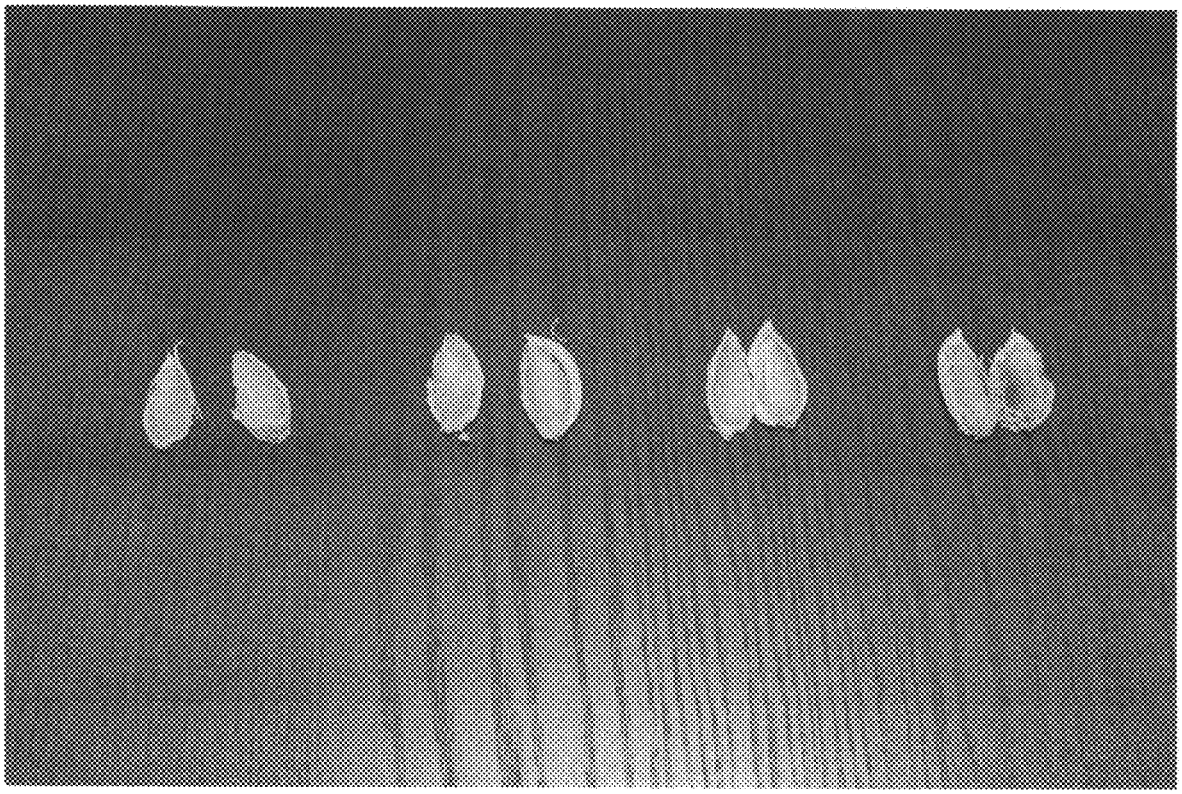
FIG. 11 is a close-up view of shells of the new variety that have been open and the kernels removed.
Figure 12:
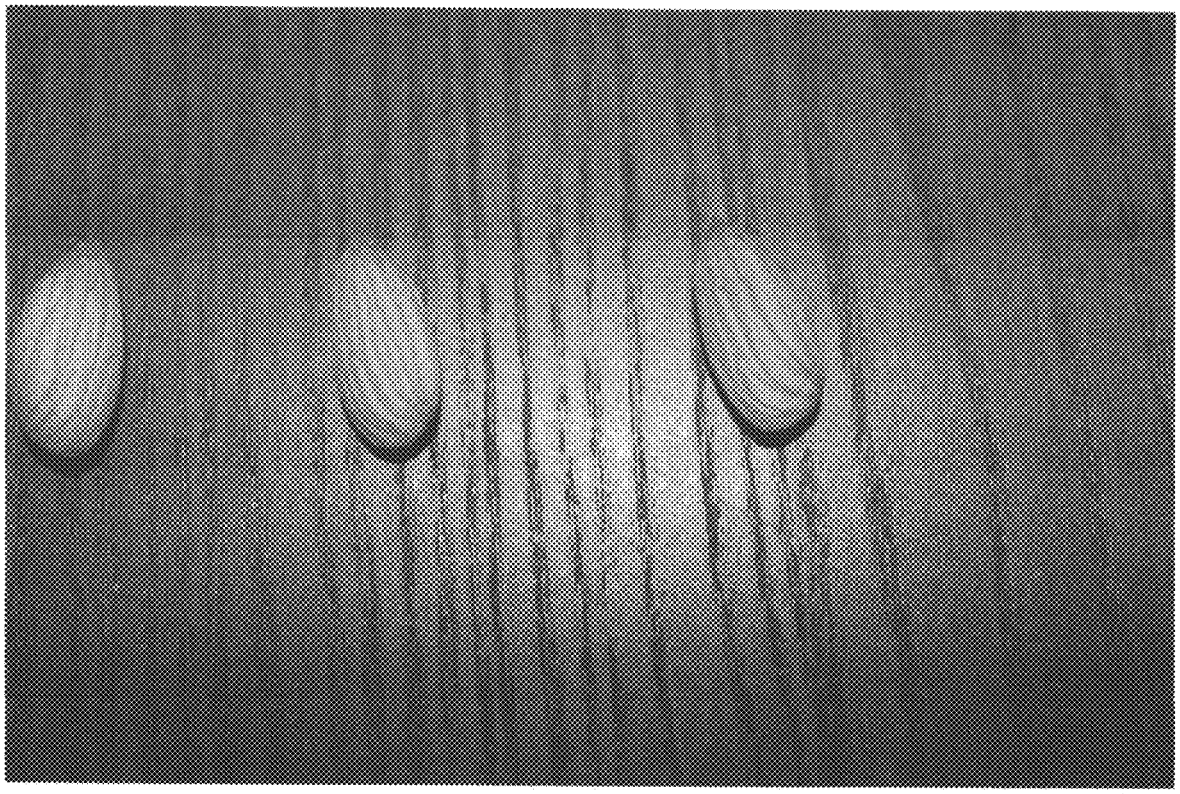
FIG. 12 is a close-up view of kernels of the new variety.
Figure 13:
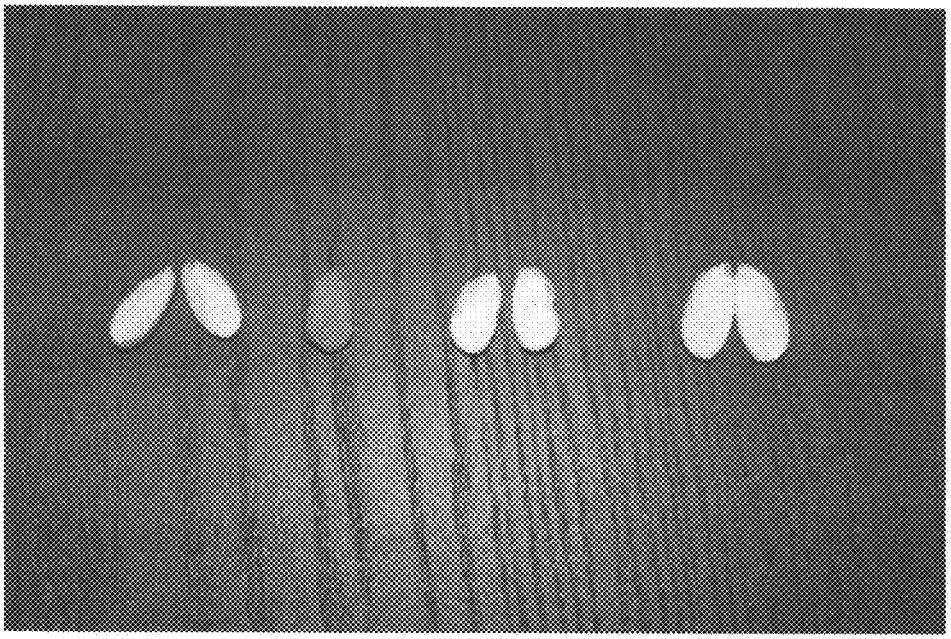
FIG. 13 is a close-up view of kernels of the new variety, some of which have been cut open.

The colors in the photographs are as true as can be reasonably obtained by conventional photographic procedures. Due to chemical development, processing and printing, the bark, leaves, nuts and flowers depicted in these photographs may, or may not, be accurate when compared to the actual specimen. For this reason, future color references should be made to the color plates and descriptions provided hereinafter.

DETAILED BOTANICAL DESCRIPTION OF THE NEW VARIETY

Referring now more specifically to the pomological characteristics of this new and distinct variety of almond tree, the following has been observed under the ecological conditions prevailing in Stanislaus County, California (San Joaquin Valley). Observations were performed at the flowering stage on Feb. 18, 2021, and just prior to the harvest stage on Aug. 18, 2021.

All major color code designations are by reference to the Dictionary of Color by Maerz & Paul, First Edition 1930. Common color names are also used.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical or other varietal characteristics as set forth, hereinafter. Therefore, this disclosure may not be relied upon to support any future legal claims including, but not limited to, breach of warranty of merchantability, or fitness for any particular purpose which is directed, in whole, or in part, to the present variety.

Tree:

*Origin*.—The present variety was discovered as an open pollinated seedling of unknown parentage growing adjacent to an orchard of 'Nonpareil' (unpatented), 'Carmel' (U.S. Plant Pat. No. 2,641), and 'Peerless' (unpatented) almond trees located in Stanislaus County, California.

*Vigor*.—Considered very vigorous.

*Hardiness*.—Considered hardy under typical San Joaquin Valley climatic conditions.

*Chilling requirement*.—Considered normal under prevailing San Joaquin Valley climatic conditions.

*Tree form*.—Considered spreading and upright in its growth pattern. For observed trees that were approximately 20 years old, when grown on unpatented 'Nemaguard' rootstock, the height of the trees were approximately 15 feet. Further, these same trees had a crown spread of approximately 22 feet.

*Productivity*.—Considered very productive. For trees that are at least 20 years old, with currently acceptable planting densities, approximately 2200 pounds of almonds on average are harvested per acre.

*Regularity of bearing*.—Considered regular for the species. No significant alternate bearing has been observed.

*Fertility*.—Self-sterile. The new variety must be cross pollinated by other almond varieties, including 'Nonpareil' (unpatented), 'Bennett-Hickman' (U.S. Plant Pat. No. 26,083), and 'Monterey' (U.S. Plant Pat. No. 3,483).

*Date of harvest*.—Late August, approximately one week after unpatented 'Nonpareil' in a normal (non-drought) year.

Trunk:

*Size*.—Considered large, approximately 49.5-65 inches in circumference when measured at a distance of about 10 inches above the surface of the earth on trees which are at least 20 years old.

*Bark texture*.—Considered moderately rough.

*Bark color*.—Medium gray (13-A-1).

*Bark lenticels*.—No lenticels visible on the trunk (rhytidome is very developed)

Branches:

*Size*.—Considered large for the species, approximately 23-38 inches in circumference when measured at a distance of approximately 12 inches above the crotch of a 20-year old tree.

*Surface texture*.—Immature branches — Considered smooth.

*Surface texture*.—Mature branches — Considered moderately rough. As wood becomes older, texture becomes rougher with accumulation of lenticels and later rhytidome.

*Bark color*.—Immature branches — First year wood is palmetto green (22-B-6).

*Bark color*.—Mature branches — Partly medium gray (13-A-1) and partly reddish-brown (7-J-10).

*Lenticels*.—Number, Size and Shape — Approximately 40-50 per square inch and 1 mm in length, and 0.5 mm in width. Shape linear. Color — Gray (55-A-1).

Leaves:

*Size*.—Considered medium for the species, approximately 105 mm in length; and about 20 mm to about 27 mm in width.

*Leaf shape*.—Considered lanceolate.

*Leaf arrangement*.—Alternate.

*Leaf apex*.—Considered acuminate.

*Leaf base*.—Considered acute to rounded.

*Leaf thickness*.—Considered normal for species.

*Leaf color*.—Upwardly facing surfaces — Moderate yellowish green (23-J-6)

*Leaf color*.—Downwardly facing surfaces — Deep yellow green (23-L-7).

*Leaf marginal form*.—Finely serrated.

*Leaf vein*.—Pinnately veined. Color — Vivid yellowish green (20-I-1).

*Leaf petiole*.—Length: about 22 mm. to about 26 mm. Leaf Petiole Thickness — about 1 mm. Leaf Petiole Color — Vivid yellowish green (20-I-1).

*Leaf stipules*.—Very inconspicuous and predominately absent.

Flowers:

*Flower depth*.—Averages about 14 mm from the base of the ovary to the tip of the stigma.

*Flower diameter*.—Average 26 mm.

*Flower fragrance*.—Moderate, honey-like.

*Date of full bloom*.—Approximately February 23.

*Bloom amount*.—Typically 3-6 flowers per cluster.

*Bloom color*.—Upper and lower petal surfaces are the same: petal base is light pink (1-G-3) while the majority of the petal is white (1-A-1).

*Petals*.—Marginal form — Considered obovate to rhomboid with widespread apex notching.

*Petals*.—Petal Number — Generally 5. Petal length — average about 14 mm. Petal width — average about 10 mm. Petal margin is undulate. Petal base is acute to 90 degree angle.

*Sepals*.—Sepal Number — Generally 5. Sepal shape — deltoid. Sepal length — average about 11.5 mm. Sepal width — average about 5 mm. Sepal apex is tapering to an acute point. Sepal margin is entire. Sepal upper surface color is pale yellowish green (18-1-6). Sepal lower surface color is strong yellow green (19-J-6) with deep reddish purple (55-L-5) venation.

*Pollen production*.—Abundant.

*Pollen color*.—Goldenrod yellow (10-L-5).

*Ovary shape*.—Ovate.

*Ovary color*.—Pale green (18-F-5) with heavy pubescence.

*Flower buds shape*.—Considered conic.

*Flower bud length* (*before petals show*).—Average about 13 mm.

*Flower bud diameter* (*before petals show*).—Average about 6.5 mm. Flower Bud color is pinkish white (49-A-2).

*Pistil number*.—1.

*Pistil length*.—Average about 11.5 mm. Anther color is light yellow (9-I-3).

*Stamen number*.—Average of about 30.

*Stamen length*.—Average about 7.5 mm to 12 mm.

*Style length*.—Average about 8 mm. Style color is pale greenish yellow (12-K-1). Stigma color is olive green (13-L-6).

*Pedicels*.—Pedicel length — average about 1.5 mm to 3.0 mm. Pedicel diameter — average about 1.5 mm. Pedicel color is sky green (18-I-5).

Crop:

*Bearing*.—On average the nut yield of the new variety is slightly greater than that of the unpatented 'Nonpareil' variety.

*Productivity*.—Considered very productive for trees that are 20 years old.

*Hull texture*.—Pubescent.

*Hull form*.—Considered ovate.

*Hull thickness*.—About 2 mm to about 3 mm.

*Hull color*.—Outer color at splitting: Strong yellow green (18-J-6); suture color at splitting: Brilliant yellow green (18-K-3).

*Dehiscence*.—Opens freely.

*Splitting*.—Complete along suture.

Nut:

*Nut size*.—Generally — Length: Average 38 mm; Width: Average 20 mm.

*Nut shape*.—Considered ovate. Similar to 'Nonpareil' and 'Monterey' (U.S. Plant Pat. No. 3,483).

*Nut thickness*.—Average 14 mm.

*Shell thickness*.—Average 3 mm.

*Outer shell*.—Form: Considered flaked.

*Inner shell*.—Considered brittle

*Shell texture*.—Smooth.

*Shell type*.—Semi-smooth.

*Color*.—Shell color at splitting varies from light tan (12-F-6) to moderate tan (12-H-7).

*Pits*.—Small, scattered and numerous.

*Wing*.—Average protrusion is 2-3 mm from surface of nut tapering at the base and apex.

Kernel:

*Size*.—Length: Average 27 mm; Width: Average 13 mm.

*Shape*.—Elongated ovate. Similar to 'Sonora' (unpatented)/'Monterey' (U.S. Plant Pat. No. 3,483).

*Kernel thickness*.—Average 8 mm at hull splitting. Stem Scar — Moderately visible as darkened spot (not raised) Apex — Shape: Considered cuspidate (terminating in a short, sharp point). Surface Texture — Heavy Smooth. Slightly ribbed along veins with slight pubescence.

*Pubescence*.—Considered slight.

*Color*.—Skin color at splitting Lt. Cocoa (13-L-9); vein color at splitting Light olive brown (15-H-12).

*Numbers of doubles produced*.—Average is approximately one percent (1.1%) which is considered low, and improves the grade of the nuts.

*Kernel flavor*.—Clean profile, less sweet than 'Carmel' (U.S. Plant Pat. No. 2,641). More favorable appearance and flavor than the 'Alm-21' (Independence) variety (U.S. Plant Pat. No. 20,295). Fresh, earthy aroma similar to 'Nonpareil' (unpatented). Good impact, good after-taste, and good consistency.

*Keeping quality*.—Considered good.

*Keeping and shipping quality*.—Considered good for the variety.

The present variety may be processed as a whole, sliced or diced product and is an excellent natural, salted or roasted nut.

Nuts of the 'PY1' variety are very well suited for roasting, seasoning, oil and flavoring, and uses that are similar to that of 'Monterey' (U.S. Plant Pat. No. 3,483) and unpatented 'Nonpareil'.

The subject variety has no known resistance to or susceptibility to any known pests or diseases.

Although this new variety of almond tree possess the described characteristics noted above as a result of the growing conditions prevailing in the Modesto area in the San Joaquin Valley of Central California, it is understood that variations of the usual magnitude and characteristics incident to changes in growing conditions, fertilization, pruning and pest control are to be expected.

What is claimed is:

1. A new and distinct variety of almond tree, named 'PY1', substantially as described and illustrated herein, that is a good pollinator for 'Monterey' (U.S. Plant Pat. No. 3,483) and unpatented 'Dallas' varieties, and which produces nuts with rare doubles that are similar to the 'Monterey' (U.S. Plant Pat. No. 3,483) and unpatented 'Nonpareil' varieties in that the crop has a fresh earthy taste, and is well suited for roasting, seasoning, oil and flavoring.

* * * * *